(12) United States Patent
Sugimura

(10) Patent No.: US 6,429,286 B1
(45) Date of Patent: Aug. 6, 2002

(54) IMMUNOREGULATORY MOLECULES FOR COSTIMULATORY SIGNAL TRANSDUCTION

(75) Inventor: Kazuhisa Sugimura, Kagoshima (JP)

(73) Assignee: Juridical Foundation The Chemo-Sero-Therapeutic Research Institute, Kumamoto (JP)

( * ) Notice: Subject to any disclaimer, the term of this patent is extended or adjusted under 35 U.S.C. 154(b) by 0 days.

(21) Appl. No.: 09/403,089

(22) PCT Filed: Jul. 23, 1997

(86) PCT No.: PCT/JP97/02540

§ 371 (c)(1),
(2), (4) Date: Oct. 15, 1999

(87) PCT Pub. No.: WO98/46739

PCT Pub. Date: Oct. 22, 1998

(30) Foreign Application Priority Data

Apr. 16, 1997 (JP) ............................................... 9-115303

(51) Int. Cl.$^7$ ............................ C07K 7/08; C07K 7/64; A61K 38/10; A61K 38/12

(52) U.S. Cl. ...................... 530/326; 530/300; 530/317; 530/321; 530/327; 530/328; 530/329; 424/184.1; 424/185.1; 424/192.1; 424/193.1; 514/2; 514/9; 514/14; 514/15; 514/16; 514/885

(58) Field of Search ................................ 530/300, 317, 530/321, 326, 327, 328, 329; 514/1, 2, 9, 14, 15, 16, 885; 424/184.1, 185.1, 192.1, 193.1

(56) References Cited

U.S. PATENT DOCUMENTS 5,811,097 A * 9/1998 Allison et al.
5,977,318 A * 11/1999 Linsley et al.

OTHER PUBLICATIONS

Walunas et al. Immunity 1994 1:405–413.*
Lenschow, et al., *Annu. rev. Immunol.*, vol. 14, pp. 233–258 (1996).
Linsley et al., *Proc. Natl. Acad. Sci. USA*, vol. 87, pp. 5031–5035 (Jul., 1990).
Azuma et al., *Nature*, vol. 366, pp. 76–79 (Nov., 1993).
Stephen et al., *J. Mol. Biol.*, vol. 248, pp. 58–78 (1995).
Yayon et al., *Proc. Natl. Acad. Sci. USA*, vol. 90, pp. 10643–10647 (Nov., 1993).
Balass et al., *Proc. Natl. Acad. Sci. USA*, vol. 90, pp. 10638–10642 (Nov., 1993).
Scott et al., *Science*, vol. 249, pp. 386–390 (Jul., 1990).
Linsley et al., *J. Ex. Med.*, vol. 174, pp. 561–569 (Sep., 1991).
Smith et al., *Method in Enzymology*, vol. 217, pp. 228–257 (1993).
Linsley et al., *J. Ex. Med.*, vol. 173, pp. 721–730 (Mar., 1991).
Waterhouse et al., *Science*, vol. 270, p. 985–988 (Nov., 1995).
De ciechi et al., *Molecular Diversity*, vol. 1, No. 2, pp. 79–86 (1995).
Linsley et al., *J. Exp. Med.*, vol. 176, No. 6, pp. 1595–1604 (Dec., 1992).
Lenschow et al., *J. Exp. Med.*, vol. 181, No. 3, pp. 1145–1155 (Mar., 1995).
Truitt et al., *J. Exp. Med.*, vol. 179, No. 3, pp. 1071–1076 (Mar., 1994).
Krummel et al., *J. Exp. Med.*, vol. 182, No. 2, pp. 459–465 (Aug., 1995).

* cited by examiner

*Primary Examiner*—Phillip Gambel
*Assistant Examiner*—Jessica H. Roark
(74) *Attorney, Agent, or Firm*—Birch, Stewart, Kolasch & Birch, LLP

(57) ABSTRACT

An immunoregulatory molecule that regulates costimulatory signal transduction through interaction with the molecules involved in costimulatory signal transduction present on antigen presenting cells and/or T cells in the activation of T cells by antigen presenting cells and a process for preparing the same are provided. Said immunoregulatory molecule comprises a peptide which has two cysteine (Cys) residues forming Cys-Cys linkage and comprises at least six amino acid residues between said Cys-Cys linkage. Said immunoregulatory molecule is obtained by screening a phage random peptide library with a monoclonal antibody to CTLA-4 on T cells involved in costimulatory signal transduction.

4 Claims, 11 Drawing Sheets

IMMUNOREGULATORY MOLECULES FOR COSTIMULATORY SIGNAL TRANSDUCTION

This application is a 371 of PCT application PCT/JP97/02540 filed Jul. 23, 1997, which claims the benefit of JP 09 115303 filed Apr. 16, 1997.

TECHNICAL FIELD

The present invention relates to an immunoregulatory molecule that regulates interactions between the molecules involved in costimulatory signal transduction following the first signal transduction involved in the activation of T cells. Said immunoregulatory molecule enables regulation of the immune system. More particularly, the present invention relates to an immunoregulatory molecule having a peptide sequence mimicking a three-dimensional structure of a target molecule wherein said immunoregulatory molecule may be obtained from a phage random peptide library by using a monoclonal antibody which inhibits binding between the molecules involved in costimulatory signal transduction and recognizes a steric structure of said molecules, and a process for preparing said immunoregulatory molecule.

BACKGROUND ART

Immunization reaction initiates with the activation of T cells. Antigens, after entering into the living body, are taken up by antigen presenting cells (hereinafter also referred to as "APC") such as macrophages or B cells. The antigen presenting cells with antigen fragments being incorporated therein then present a complex of antigens (Ag) and major tissue compatibility antigen (MHC) class I or class II on the cellular surface. This MHC/Ag complex is recognized by the T cell receptor (TCR)/CD3 complex on T cells to thereby transmit the first signal into the T cell.

The second signal is also called costimulatory signal and is transmitted into T cells through interaction between the cell adhesion molecules expressed on the cellular membranes of both T cells and APC. Both the first and second signals are necessary for the activation of T cells. It has been observed that inhibition of the second (costimulatory) signal transduction inactivates T cells thereby to lead anergy, i.e. lack of immunological responsiveness. It is believed that the costimulatory signal is transmitted through interaction between CD80 (also called "B7-1" or "B7/BB1") and CD86 (also called "B7-2" or "B70") expressed on APC and their corresponding receptors expressed on T cells, CD28 and cytotoxic T lymphocyte associated antigen (CTLA-4) (Lenschow, D. J. et al., Annu. Rev. Immunol. 14, 233–258, 1996).

CD28 molecule is a glycoprotein expressed on T cells. It is elucidated that CD28 molecule acts as a costimulatory receptor which promotes T cell growth and production of various cytokines upon stimulation from TCR. CTLA-4 molecule is known to be quite similar to CD28 in both its structure and function. In CTLA-4-knockout mice, T cells proliferate in the spleen or lymph nodes, T cell infiltration occurs in many organs including cardiac muscle, thyroid, spleen, etc. and the mice die of autoimmune diseases, suggesting that CTLA-4 is a negative regulator of T cell response.

As a ligand of CD28/CTLA-4, Linsley et al. identified CD80 molecule in 1990 (Proc. Natl. Acad. Sci USA, 87, 5031–5035) and Azuma et al. identified CD86 molecule in 1993 (Nature, 366, 76–79). CD80 is a transmembrane glycoprotein with a short intracellular region having a signal transduction domain which is classified into Ig superfamily. Like CD80, CD86 is also a transmembrane glycoprotein classified into Ig superfamily. However, unlike CD80, CD86 bears three domains of potential protein kinase C dependent phosphorylation in the intracellular region, suggesting that it is capable of signal transduction. Both CD80 and CD86 are involved in growth, cytotoxic activity and differentiation in the thymus, of T cells. CD28 or CTLA-4 molecule has an ability to bind to CD80 or CD86 molecule and it is believed that the stages when these molecules are expressed or interaction of these molecules may induce the activation or inhibition of T cells to ultimately affect a whole immune system.

As described above, CD28, CTLA-4, CD80 and CD86 molecules play an extremely important role in exerting various immunological functions such as antigen response of T cells or interactions of B cells. These molecules undertake major parts of the costimulatory signal transduction following the first signal transduction through interaction between MHC/Ag complex and TCR/CD3 complex. Thus, one can expect that a whole immune system may be regulated through regulation of the costimulatory signal transduction. As one of such attempts, antibodies to CD28 and CTLA-4 molecules were used wherein T cells previously stimulated with anti-CD3 antibody were reacted with anti-CTLA-4 or anti-B7 antibodies in the presence of anti-CD28 antibody thereby to enhance the activation of T cells by anti-C28 antibody by a little less than 3-fold (Matthew F. et al., J. Exp. Med. 182, 459–465, 1995).

Transduction of information within the living body is made as a signal transduction mediated by binding between a receptor molecule expressed on the cellular surface and its corresponding ligand molecule. Receptor and ligand molecules are complementary to each other and can bind together when they are in a key-and-keyhole relationship. However, the most crucial site involved in binding resides within a small portion of ligand. Thus, elucidation of the structure of said site for interaction enables inhibition or enhancement of binding between receptor and ligand.

To elucidate the structure of either of sites for interaction in a certain receptor-ligand system, a peptide scanning procedure has conventionally been used wherein peptides of an appropriate size are synthesized over a whole length of amino acid sequence of said protein and are studied for their binding capacity or binding inhibitory activity to screen the site for interaction. Alternatively, contribution of each amino acid residue to interaction was determined by one-by-one amino acid substitution by site-directed mutagenesis, or amino acid residues involved in protein-protein interaction were identified by photoaffinity procedure.

More recently, there has been used a screening with a phage random peptide library as developed by Scott et al. (Science, 249, 386–390, 1990) wherein genes encoding random peptide molecules are inserted into the gene (geneIII) of pIII molecule being consisted of phage, pIII molecule are expressed together with random peptide molecules incorporated therein on fd-tet phage (filamentous single stranded DNA phage), a phage random peptide library is prepared, phages bound are selected by, for example, panning, and said pIII gene is sequenced to determine the interaction site. According to this procedure, a population of as many as several 105 kinds of peptides may be obtained more easily than chemical synthesis and moreover amplification is also possible as required.

Using a phage random peptide library, there has been attempted to identify interaction sites on a target molecule.

Typically, a ligand or a receptor is directly bound to a plate as a solid phase and a phage random peptide library is screened for desired interaction sites by panning. However, this procedure provides a large number of phage clones capable of binding to the target molecule, most of which phage clones however cannot bind to the critical binding site that regulates a ligand-receptor interaction. Thus, those phages having a peptide sequence capable of regulating a ligand-receptor interaction could only be obtained with much difficulty and poor efficiency.

When a phage library is screened with antibodies having definite antigen specificity, effective binding peptides have been obtained comparatively efficiently. For example, for determining epitopes on p53 molecule, anti-p53 monoclonal antibody was used with a random peptide library of various lengths of amino acid sequence wherein peptides having an amino acid sequence highly homologous to that of p53 molecule are screened with anti-p53 monoclonal antibody and therefrom the epitopes were identified (Stepheni, C. W. et al., J. Mol. Biol., 248, 58–78, 1995). Also, a phage random peptide library of a sequence of six amino acid residues was screened with anti-bFGF antibody to give peptides having similar amino acid sequence to that of bFGF. It was reported that synthetic peptides prepared by elongating these screened peptides to those having eight amino acid residues inhibited binding between bFGF and its receptor FGFR-1 (Yayon, A. et al., Proc. Natl. Acad. Sci. USA, 90, 10643–10647, 1993). When motifs capable of binding to antibodies recognizing conformational epitopes on acetylcholine receptor were screened with a phage random peptide library of a sequence of six amino acid residues, peptides were obtained which had a non-homologous amino acid sequence to that of acetylcholine receptor but were capable of binding to this antibody. However, whether these peptides bind to acetylcholine is not referred to (Balass, M. et al., Proc. Natl. Acad. Sci. USA, 90, 10638–10642, 1993).

As mentioned hereinabove, in order to regulate the immune reaction through regulation of molecules involved in costimulatory signal transduction, antibodies to B7 or CTLA-4 molecules have been used. However, the effect of these antibodies, i.e. enhancement in the activation of T cells by a little less than 3-fold, is not sufficiently high. Furthermore, no specific antigens were used in their experiment and hence the effect was not proved in in vivo immune reaction. Other than antibodies, there is no report to attempt to design small molecules involved in costimulatory signal transduction for use as a medicament.

For designing such small molecules, the conventional approach was to first analyze sites associated with interaction of target molecules and to synthesize peptides based on the determined amino acid sequence of said sites to thereby design desired small molecules. However, even if an amino acid sequence of sites associated with protein-protein interaction is determined by the conventional analytical procedure and oligopeptides are prepared based on the obtained primary amino acid sequence, it was difficult to design small molecules which can act in replace of target molecules. That is, sites associated with interaction of protein molecules having crucial function are defined by a three-dimensional structure and hence amino acid residues involved in interaction are dispersed within a primary amino acid sequence although they gather together as a three-dimensional structure is constructed. Thus, from oligopeptides prepared based on a primary amino acid sequence of sites associated with interaction, reconstruction of a three-dimensional structure of said sites was technically restricted and designing small molecules with effective function was difficult.

In case of screening with a phage random peptide library, screening by panning with a receptor or a ligand directly bound to a solid phase could provide those phages having a specific peptide sequence capable of regulating receptor-ligand interaction only with quite poor efficiency and difficulty. The screening with a protein molecule having a relatively definite antigen specificity such as an antibody is merely used for determining a primary amino acid sequence of a target molecule to which said antibody binds or for determining motifs having high homology with said primary amino acid sequence. In the absence of such homology, however, peptide sequences to which the antibody could merely bind were obtained. That is, there has been no report that molecules mimicking a three-dimensional structure of a target molecule to which an antibody binds could be obtained without depending on a primary amino acid sequence thereof. Much less, there is no report that small molecules capable of regulating the immune system could be obtained by targeting CD80 and CD86 expressed on APC and their corresponding receptors, CD28 and CTLA-4 expressed on T cells. Also, there is no report that such small molecules could be designed without depending on a primary amino acid sequence of the target molecules.

DISCLOSURE OF INVENTION

The present invention provides an immunoregulatory molecule that regulates interactions between molecules involved in costimulatory signal transduction following the first signal transduction mediated by MHC/Ag complex and TCR/CD3 complex involved in the activation of T cells. Said immunoregulatory molecule enables regulation of the immune system. More particularly, the present invention provides an immunoregulatory molecule having a peptide sequence mimicking a three-dimensional structure of a target molecule wherein said immunoregulatory molecule inhibits binding between molecules involved in costimulatory signal transduction and may be obtained from a phage random peptide library with the use of a monoclonal antibody recognizing a steric structure of said molecules, and a process for preparing said immunomodulating molecule.

BEST MODE FOR CARRYING OUT THE INVENTION

Figure 1:
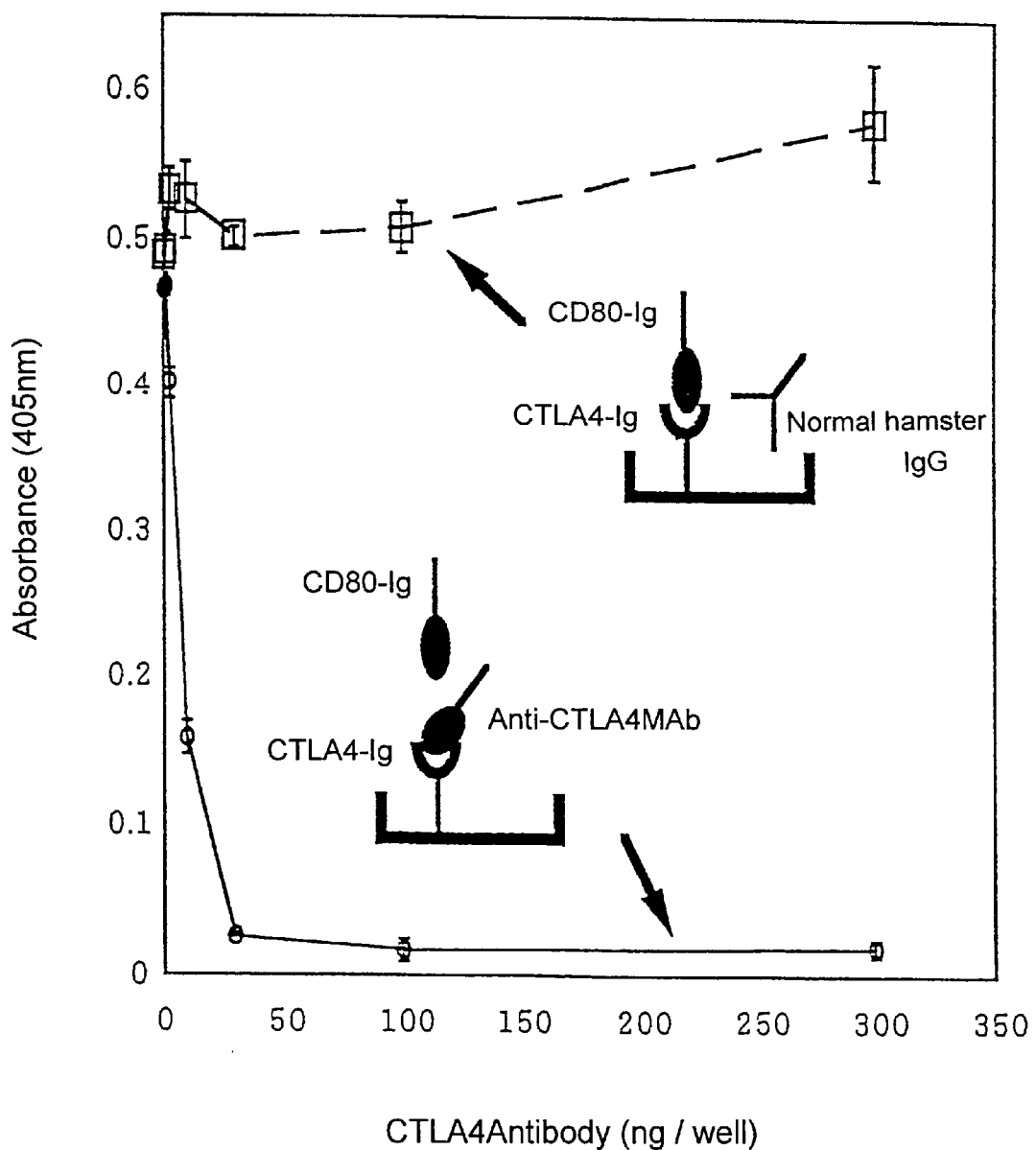
FIG. 1 shows specificity of anti-mouse CTLA-4 monoclonal antibody used in screening of a phage random peptide library.

When a monoclonal antibody to a molecule "A" capable of inhibiting binding between molecules "A" and "B" and of recognizing a steric structure of the molecule "A" is used for isolating phage clones bound to said antibody from a phage random peptide library, the antibody acts as a "template" of a three-dimensional structure of binding sites on the molecule "A", namely as binding sites on the molecule "B". Thus, the antibody binds to those clones presenting on their surface a structure mimicking a three-dimensional structure of the binding sites on the molecule "A".

On the other hand, when the molecule "B" per se is conventionally used for the purpose of screening, phage clones bound to sites on the molecule "B" being irrelevant to the molecular interaction between "A" and "B" are also screened since there are a large number of sites on the molecule "B" which can be bound to phage clones. As such, screening with this procedure was quite inefficient. However, using an anti-molecule "A" monoclonal antibody recognizing a steric structure of sites on the molecule "A" involved in molecular interaction between "A" and "B", the steric structure of such sites alone can be extracted and hence a range of sites to be targeted can extremely be narrowed. In this respect, screening efficiency can drastically be increased.

In order to retain a steric structure of peptides, peptides are kept on phages without being released therefrom. The phage clones are then further screened for their binding capacity to the molecule "B" to thereby allow selection of phage clones bearing a peptide sequence of much close steric structure to that of the molecule "A". Since such peptide sequences exhibit a much close structure to that of the molecule "A", agonistic or antagonistic activities of the molecule "A" can be elucidated by screening with bioassay, and the like. Furthermore, since phage clones with the thus screened peptide sequences have a much close steric structure to that of the molecule "A", agonist or antagonist of a molecule "C" rather than the molecule "A" may also be obtained wherein said molecule "C", belonging to a superfamily of molecule "A", is distinct from the molecule "A" but has a close steric structure to is that of the molecule "A".

Using the procedures as mentioned above, for targeting CD80/CD86 and CD28/CTLA-4 involved in costimulatory signal transduction as well as unknown molecules having a close steric structure to that of these molecules, small molecules regulating the immune system can be prepared without depending on a primary amino acid sequence. Thus, peptide sequences enhancing the activation of T cells were obtained as one aspect of the present invention.

The term "immunoregulatory molecule" as used herein is referred to a molecule targeting the molecules involved in costimulatory signal transduction following the first signal transduction. The term "molecules involved in costimulatory signal transduction" as used herein is referred to CD80/CD86 expressed on APC and the corresponding receptors CD28/CTLA-4 expressed on T cells as well as unknown molecules having a close steric structure of that of these molecules. The immunoregulatory molecules of the present invention may be obtained by screening a phage random peptide library presenting 108 or more of random peptide sequences with a length of at least eight amino acid residues while peptides are kept on phages, using a monoclonal antibody which inhibits binding between molecules involved in costimulatory signal transduction is following the first signal transduction and recognizes a steric structure of said molecules.

The immunoregulatory molecule of the present invention binds to an antibody to CTLA-4 which is involved in costimulatory signal transduction and expressed on T cells. From viewpoint of an amino acid sequence, the immunoregulatory molecule of the present invention is a molecule with a length of at least eight amino acid residues which has two Cys residues to form an intramolecular S—S bonding and comprises at least six amino acid residues between these Cys residues. The amino acid sequence of the immunoregulatory molecule of the present invention is also characterized in that it has little homology with that of CTLA-4 molecule.

Typical examples of the immunoregulatory molecule of the present invention include F2 as depicted in SEQ ID NO: 4 and F6 as depicted in SEQ ID NO: 8.

The immunoregulatory molecule of the present invention may be used as being fixed on a carrier, as being incorporated into a protein, or as a free peptide prepared by a peptide synthesis, as far as its steric structure is retained based on peptide sequence information of F2 and F6 obtained from phage clones. Furthermore, based on F2 and F6 as a prototype, the peptide sequences of these compounds may be modified by deletion, substitution or addition insofar as the steric structure of F2 or F6 is retained.

The monoclonal antibody used in the present invention may be an antibody derived from any animal species having an ability to inhibit binding between the molecules involved in costimulatory signal transduction. The antibody of the present invention is not limited to a specific subclass or isotype but preferably recognizes conformational epitopes. For anti-CTLA-4 antibody to CTLA-4 expressed on T cells, UC10-4F10-11 monoclonal antibody (manufactured by PharMingen) is used herein but the present invention is not limited thereto. For example, any monoclonal antibody which can inhibit binding between CTLA-4 and CD80/CD86 or binding between CD28 and CD80/CD86 and recognizes conformational epitopes, e.g. anti-CD28 antibody, may be used. The term "antibody recognizing conformational epitopes" as used herein is referred to an antibody which recognizes a steric structure of epitopes, or an antibody whose antigen binding sites represent a steric structure of a corresponding ligand. Specifically, as the antibody recognizing conformational epitopes, there are referred to an antibody capable of binding to a native antigen in immunoprecipitation but not to a denatured antigen, or an antibody not capable of binding to an antigen in Western blot analysis under reduced condition, or an antibody not capable of binding to a linear peptide synthesized based on an amino acid sequence of epitopes.

A phage random peptide library used in the present invention may be phage vectors of any kind which represent peptides of random sequences on the phage surface. Peptides of random sequences to be inserted into phages may be preferably in a length of at least eight amino acid residues, and more preferably in a length of at least fifteen amino acid residues. Peptides of random sequences may be inserted into any protein constituting phages as far as the peptides are represented on the phage surface but preferably into pIII molecule. By inserting peptides of random sequences in a length of at least fifteen amino acid residues at the site between the 4th Ala and 5th Gly counted from the N-terminus of pIII molecule (corresponding to the amino acid residues No. 22 and No. 23 in the amino acid sequence of SEQ ID NO: 1, respectively), effects of amino acid sequences flanking a motif of peptides at both ends on a three-dimensional structure of said motif may be minimized.

The present invention initiates with screening of a phage random peptide library using the anti-CTLA-4 antibody as mentioned above. For screening, a usual panning procedure with the antibody immobilized on a plate or an affinity column procedure with the immobilized antibody may be used. Desired phage clones may be enriched after repeating a step of a panning, a phage recovery, a phage growth and a panning for three times or more. Phage clones having peptide sequences capable of binding to anti-CTLA-4 antibody may be obtained as screened above. The thus obtained phage clones may be usually classified into several subpopulations of clones based on distinction of binding capacity to the antibody or features of amino acid sequences of peptides retained within phage clones. Sequencing of phage clones may be easily carried out by the conventional procedure such as dideoxy method.

The phage clones as classified above are further screened for selecting those clones with peptide sequences having T cell regulating activities in in vitro or in vivo assay systems. For example, phage clones screened with anti-CTLA-4 antibody are expected to act as the CTLA-4 molecule, and hence, may be further screened by an assay system wherein binding of these phage clones with the corresponding receptors for the CTLA-4 molecule, CD80/CD86, is determined. Alternatively, such phage clones may also be screened in a bioassay system wherein the interaction between the molecules involved in costimulatory signal transduction can be determined in the actual immune reaction. The bioassay system as used herein may be any procedure which can determine a degree of the activation of T cells. For example, measurement of an amount of cytokine produced as a result of the activation of T cells may be used. Preferably, T cells or antigen presenting cells from animals immunized once with an antigen are stimulated with phage clones having peptide sequences alone or with the antigen and phage clones having peptide sequences and then a degree of the activation of T cells is determined by measuring a take-up of $^3$H thymidine.

By subjecting the phage clones as classified above into an assay system reflecting the actual immune response, phage clones having peptide sequences capable of regulating T cells through currently unknown mechanism may possibly be obtained. A peptide having an amino acid sequence of F6 (SEQ ID NO: 8) represents a preferable example of such phage clones. It is believed that the phage bearing F6 sequence may possibly interact with certain unknown immune-related factor which is distinct from, but is similar to, CD80 or CD86. For screening such peptide sequences, phage clones are preferably assayed as they represent peptides on their surface. In case of peptide sequences wherein their steric structure is crucial, such steric structure cannot be retained any more in many cases if free peptides are released from phages. However, if peptides can be synthesized while retaining their steric structure based on peptide sequence information obtained from phage clones, then peptides alone may be subjected to the screening system as mentioned above.

According to the procedures as explained above, phage clones having peptide sequences which can bind to CD80/CD86 molecules and can activate T cells may be obtained and preferably includes F2 (SEQ ID NO: 4). Phage clones having peptide sequences which do not bind to CD80/CD86 molecules but can activate T cells may also be obtained and preferably includes F6 (SEQ ID NO: 8).

The immunoregulatory molecule of the present invention can regulate T cells either positively or negatively depending on the expression of the molecules involved in costimulatory signal transduction. For example, when CD28 acts mainly, the immunoregulatory molecule thereto can act as an immunosuppressive factor. On the other hand, when CTLA-4 acts mainly, the immunoregulatory molecule thereto can act as an immunologically activating factor. For example, the typical immunoregulatory molecule of the present invention, F2 and F6, may drastically (from 5-fold to 10-fold) enhance the antigen-specific proliferation of T cells.

The regulatory activity of the immunoregulatory molecule of the present invention may be independent of a kind of antigens. That is, the immunoregulatory molecule acts in an antigen non-specific manner, and hence, can regulate immune reactions for any antigen present in association with said molecule. For exerting the regulatory activity, the immunoregulatory molecule may either be present on the same molecule as an antigen or may separately be used from an antigen.

The immunoregulatory molecule of the present invention regulating interaction between the molecules involved in costimulatory signal transduction can ultimately regulate immune reactions, and hence, may be applied to any disease associated with immune reactions. Most preferable use includes vaccine, or as an immunologically activating agent in antigen-specific immunotherapy, or as an immunosuppressive agent in an allergic reaction.

Apart from the molecules involved in costimulatory signal transduction, the present invention also provides a novel method for designing a small molecule capable of regulating interactions between high molecular weight biomolecules in general, e.g. a receptor molecule and its ligand molecule, or an enzyme molecule and its substrate protein, etc. The method of the present invention allows for molecularly designing a small molecule regulating interaction between high molecular weight biomolecules without depending on a primary amino acid sequence, and hence, is useful for molecularly designing an agonist or antagonist of a receptor or a ligand. Since this method may be applied to any high molecular weight biomolecules, peptide motifs to be identified by this novel technology will greatly accelerate the development of novel drugs. Furthermore, the development of drugs is not all that is accelerated but medical materials utilizing selective adhesion technique, functional materials such as drug delivery system (DDS), as well as general applied techniques utilizing specific binding between molecules, may also greatly be accelerated by the method of- the present invention.

EXAMPLE

The present invention is illustrated in more detail hereinbelow by means of Examples but is not construed to be limited thereto.

Example 1
Phage Random Peptide Library

Smith et al. reported a phage random peptide library wherein random genes for peptides of a length as desired are inserted into a gene (geneIII) coding for pIII protein occurring at the tip of phages and wherein phages express pIII protein bearing peptide molecules while phages continuously infect (G. P. Smith, Science, Vol. 249, p.386–390 (1990)). A primary amino acid sequence of pIII protein is shown in SEQ ID NO: 1. Genes for random amino acid sequences may be inserted at the site between the amino acids No. 22 Ala and No. 23 Gly in this primary sequence to express peptides as a fusion protein with pIII. With this procedure, as much as several 108 peptides may easily be prepared as compared to the chemical synthesis and amplification-of any gene is also possible as desired.

A phage random peptide library as used herein for screening is one prepared by Nishi, Saya et al. (T. Nishi, Experimental Medicine, Vol. 11, p.95–100 (1993)) which is prepared as described by Smith et al. This phage random peptide library was prepared wherein genes for random amino acid sequences in a length of 15 amino acid residues are inserted between the amino acids No. 22 Ala and No. 23 Gly in SEQ ID NO: 1 within a gene (geneIII) coding for pIII protein occurring at the tip of phages and wherein phages express peptides of 15 amino acid residues as fused with pIII protein. This phage library (fd-tet) expressing random peptide molecules of fifteen amino acid residues within pIII protein of phages was used herein for screening.

Example 2
Activity of Antibodies Used for Screening

An object of the present invention is to provide phage clones having peptide sequences which exhibit immunoregulatory activity through interaction with CD80, CTLA-4 or molecules associated with these molecules. Thus, the phage random peptide library as in Example 1 was screened with anti-mouse CTLA-4 monoclonal antibody (UC10-4F10-11 purchased from PharMingen) to isolate phage clones specifically bound to this antibody. It is believed that motifs of fifteen amino acid residues contained in pIII of phages specifically bound to this antibody have a similar structure to that of the site on CTLA-4 molecule recognized by this antibody. Since this site is involved in interaction with the ligand as explained hereinbelow, these motifs obtained from phages also recognize CD80/CD86 molecule and thus may influence interaction between CTLA-4 molecule and CD80/CD86 molecule or may transmit certain signal to CD80/CD86 molecule.

For determining specificity of the antibody used herein for screening, the following procedures were carried out. CTLA-4-Ig and CD80-Ig chimeric molecules used herein were prepared by introducing pCDM8 expression plasmid (gift from Hokkaido University, Immunology Laboratory), wherein chimeric gene fragments of CTLA-4-Ig and CD80-Ig prepared as described by Linsley et al. (J. Ex. Med. Vol. 174, p.561–569 (1991)) were incorporated into pCDM8, into COS7 cells, culturing the cells for 72 hours, and purifying the chimeric molecules from culture supernatant using Protein A Sepharose column (manufactured by Pharmacia).

To 96 well EIA plate (Sumitomo Bakelite, Tokyo) was added 50 μl/well of CTLA-4-Ig (200 ng/ml) diluted with 50 mM Tris-HCl, pH 7.5, 150 mM NaCl (TBS) supplemented with 0.02% $NaN_3$. The plate was incubated at 37° C. for 1 hour and then washed with 50 mM Tris-HCl, pH 7.5, 150 mM NaCl supplemented with 0.5% Tween 20 (TBST). To each well was added 250 μl of 1% bovine serum albumin (BSA) and the plate was incubated at 37° C. for 1 hour for masking. After washing of each well with TBST, anti-mouse CTLA-4 monoclonal antibody diluted to various concentrations with TBS was added at 100 μl/well and the plate was incubated at 37° C. for 1 hour and washed with TBST. Thereafter, biotin-labeled mouse CD80-Ig diluted to 200 ng/ml with TBS was added at 50 μl/well and the plate was incubated at 37° C. for 1 hour and washed with TBST.

Finally, to each well was added alkaline phosphatase-labeled streptavidin (Leinco Technologies Ltd., Missouri) diluted to 100-fold with TBS and the plate was incubated at 37° C. for 1 hour and washed with TBST. Then, the substrate sodium p-nitrophenylphosphate hexahydrate (Wako Junyaku, Osaka) was added and absorbance at 405 nm was measured. In place of the anti-mouse CTLA-4 monoclonal antibody, a hamster antibody of the same isotype (obtained by dialyzing ammonium sulfate (33–55%) saturated fractions of hamster serum against PBS) was used as a negative control. As a result, it was found that the anti-mouse CTLA-4 monoclonal antibody completely inhibited binding between CTLA-4-Ig and CD80-Ig as shown in FIG. 1.

Example 3
Panning of Phage Clones Binding to Anti-CTLA-4 Antibody

Using the anti-CTLA-4 antibody which inhibited binding between CTLA-4-Ig and CD80-Ig as shown in Example 2, panning of the phage random peptide library as described in Example 1 was carried out by the following procedures.

Each of plastic plates with 35 mm diameter (Iwaki Glass, Tokyo) was coated with 1 ml of the anti-mouse CTLA-4 monoclonal antibody at 10 μg/ml and reacted with the phage random peptide library ($1.2 \times 10^{12}$ TU) at 4° C. for 16 hours. These plates were washed with TBST to remove unbound phages and then added with 0.1 N HCl-Glycine, pH 2.2 (1 mg/ml BSA, 0.1 mg/ml phenol red (Gibco, New York)) to elute phages specifically bound to the anti-mouse CTLA-4 monoclonal antibody. The bound phages were recovered and neutralized with Tris-HCl, pH 9.1. *E. coli* K91 kan was infected with the obtained phages and grown. With a decreased amount (5 μg/ml, 1 μg/ml) of the anti-mouse CTLA-4 monoclonal antibody used for panning, the above procedures were repeated for a total of three times to select phages bound more strongly and specifically with the anti-mouse CTLA-4 monoclonal antibody.

Figure 2:
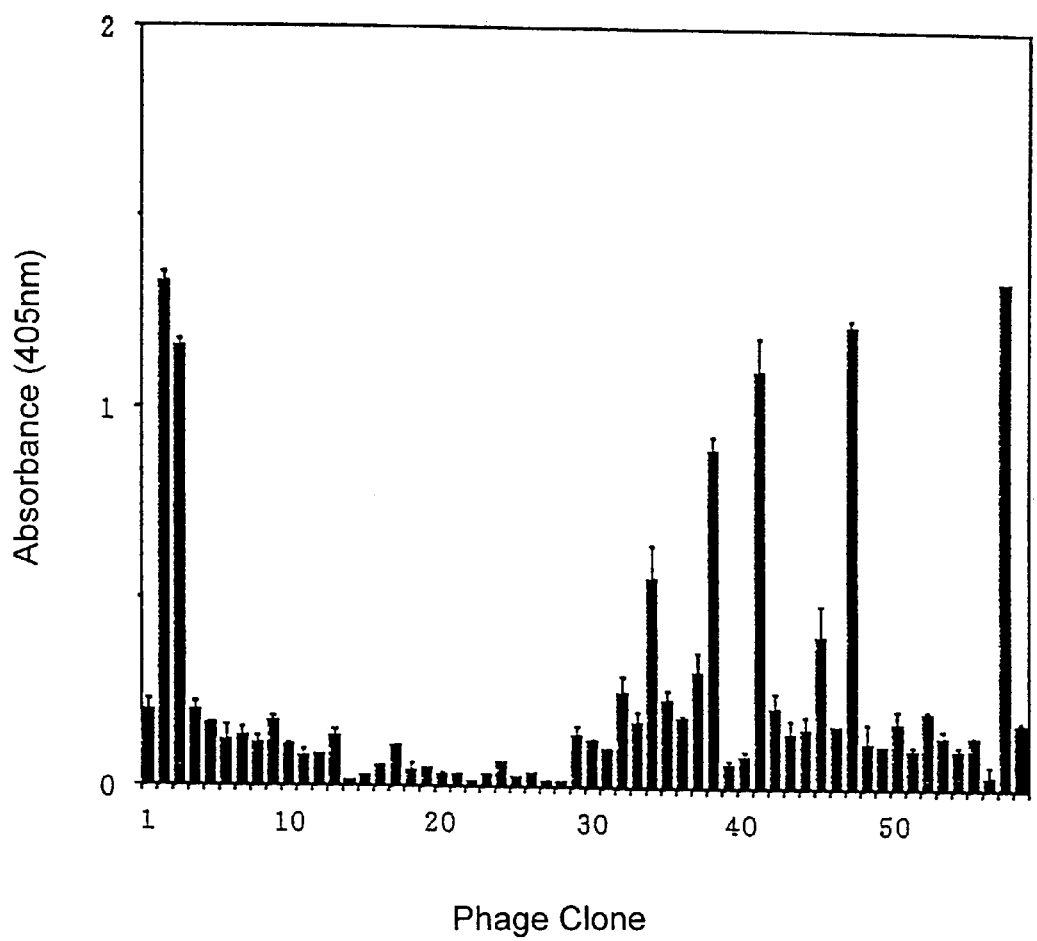
FIG. 2 shows reactivity of 58 phage clones, obtained by panning phage clones bound with anti-CTLA-4 antibody, with anti-mouse CTLA-4 monoclonal antibody.

The obtained 58 phage clones were subjected to primary screening with ELISA. A 96 well ELISA plate (Sumitomo Bakelite, Tokyo) was coated with each phage ($4 \times 10^9$ virions/well/40 μl) purified as described by Smith et al. (G. P. Smith, Method in Enzymology, Vol. 217, p.228–257 (1993), Academic Press) at 4° C. overnight. The plate was washed with TBST and was blocked with 100 μl/well of 50 mM Tris-HCl, pH 7.5, 150 mM NaCl supplemented with 0.02% $NaN_3$ and 1% BSA at room temperature for 2 hours. After washing with TBST, the plate was added with the anti-mouse CTLA-4 monoclonal antibody (200 ng/ml/well/ 100 μl) and reacted at room temperature for 1 hour. After washing with TBST, the plate was reacted with anti-hamster IgG antibody (Zymet, California) labeled with alkaline phosphatase diluted to 250-fold with TBS at room temperature for 1 hour. After washing, the plate was added with the substrate sodium p-nitrophenylphosphate hexahydrate (Wako Junyaku, Osaka) was added and absorbance at 405 nm was measured. As a result, 21 phage clones were proved to react with the anti-mouse CTLA-4 monoclonal antibody (FIG. 2).

Example 4
Determination of Amino Acid Sequence of Peptides Inserted in Phages Clones after Panning A nucleic acid sequence for peptides inserted in 21 phage clones obtained in Example 3 was determined wherein DNAs were recovered from each of the phage clones as described by Smith et al. (G. P. Smith, Method in Enzymology, Vol. 217, p.228–257 (1993), Academic Press) and were sequenced with 373A–36S DNA Sequencer (Applied Biosystems) using a synthetic DNA as shown in SEQ ID NO: 2 as a primer. The primer used corresponds to a region of from the amino acids No. 37 Pro to No. 41 Asn in the amino acid sequence as shown in SEQ ID NO: 1.

As a result of sequence analysis of nucleotide sequence, it was proved that amino acid sequence motifs of these phage clones inserted at the site between the amino acids No. 22 Ala and No. 23 Gly of pIII protein as shown in SEQ ID NO: 1 could be classified into six kinds of amino acid sequence motifs as shown in SEQ ID NOs: 3 to 8. These amino acid sequences were compared with that of CTLA-4 to reveal no homology. These amino acid sequence motifs are shown in Table 1. These amino acid sequence motifs are referred to as F1 (SEQ ID NO: 3), F2 (SEQ ID NO: 4), F3 (SEQ ID NO: 5), F4 (SEQ ID NO: 6), F5 (SEQ ID NO: 7) and F6 (SEQ ID NO: 8), respectively, and analyzed hereinbelow.

TABLE 1

F1: Gly Leu His Ser Arg Cys His Ile Gly Arg Asp Cys Ser Ser Ala

F2: Gly Phe Val Cys Ser Gly Ile Phe Ala Val Gly Val Gly Arg Cys

F3: Ser Cys Val Phe His His Ser Gly Arg Tyr Trp Gly Arg Cys Val

F4: His Tyr Gly Asp Cys Arg Tyr Asp Leu Gly Ser Cys Arg Gly Ala

F5: Ala Cys Val Met Tyr Asp Phe Val Leu Arg Gly Met Cys Ala Arg

F6: Ala Pro Gly Val Arg Leu Gly Cys Ala Val Leu Gly Arg Tyr Cys

Figure 3:
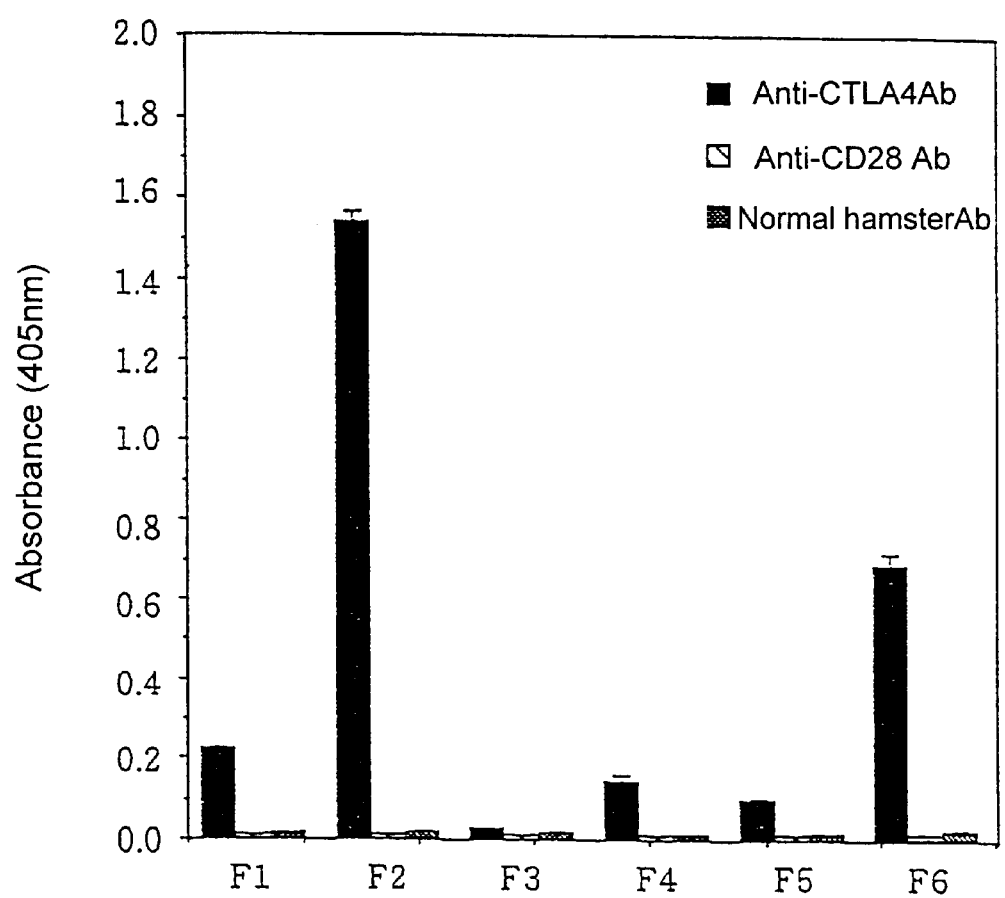
FIG. 3 shows a binding capacity of six phage clones with anti-mouse CTLA-4 monoclonal antibody.

Example 5
Binding Specificity of Each Motif with Anti-Mouse CTLA-4 Monoclonal Antibody Whether each of the motifs as shown in Example 4 specifically binds to the anti-mouse CTLA-4 monoclonal antibody was investigated. A degree of specificity was determined by ELISA as described in Example 3. As a negative control, anti-mouse CD28 antibody (Phamingen, San Diego), having the same isotype with the anti-mouse CTLA-4 monoclonal antibody, and hamster IgG were used. Anti-hamster IgG antibody was used as a detection antibody. As a result, it was found that phages expressing F2 sequence and F6 sequence reacted most strongly with the anti-mouse CTLA-4 monoclonal antibody. Phages expressing F1, F4 or F5 sequence reacted weakly and phage expressing F3 sequence reacted more weakly with the antibody (FIG. 3). *E. coli* producing the phage expressing F2 sequence and the phage expressing F6 sequence have been deposited by the applicant in accordance with the Budapest Treaty as *Escherichia coli* F2 [FERM BP-6009] and as *Escherichia coli* F6 [FERM BP-60103], respectively, at National Institute of Bioscience and Human-Technology Agency of Industrial Science and Technology, 1–3, Higashi 1-chome, Tsukuba-shi, Ibaraki-ken, 305, Japan, on Apr. 14, 1997 (original deposition date: transferred from FERM P-16192 and FERM P-16193, respectively, to the deposition under the Budapest Treaty on Jul. 4, 1997).

Example 6
T Cell Growth Enhancing Activity of Each Phage

As described in Example 5, the phages expressing the six kinds of amino acid sequence motifs obtained herein have a binding activity to the anti-mouse CTLA-4 monoclonal antibody. Thus, it is expected that these phages may behave like CTLA-4 molecule as a homologue thereof although their amino acid sequences do not exhibit homology with that of the anti-mouse CTLA-4 monoclonal antibody. First, effects of these phages on the growth of T cells were investigated in mice.

BALB/c mice (6 weeks old; four animals per group) were used in an experiment and the phages were purified as described by Smith et al. (G. P. Smith, Method in Enzymology, Vol. 217, p.228–257 (1993), Academic Press). An amount of the phages was measured using protein assay kit (BioRad) with bovine serum albumin as a standard and expressed as a protein concentration.

Figure 4:
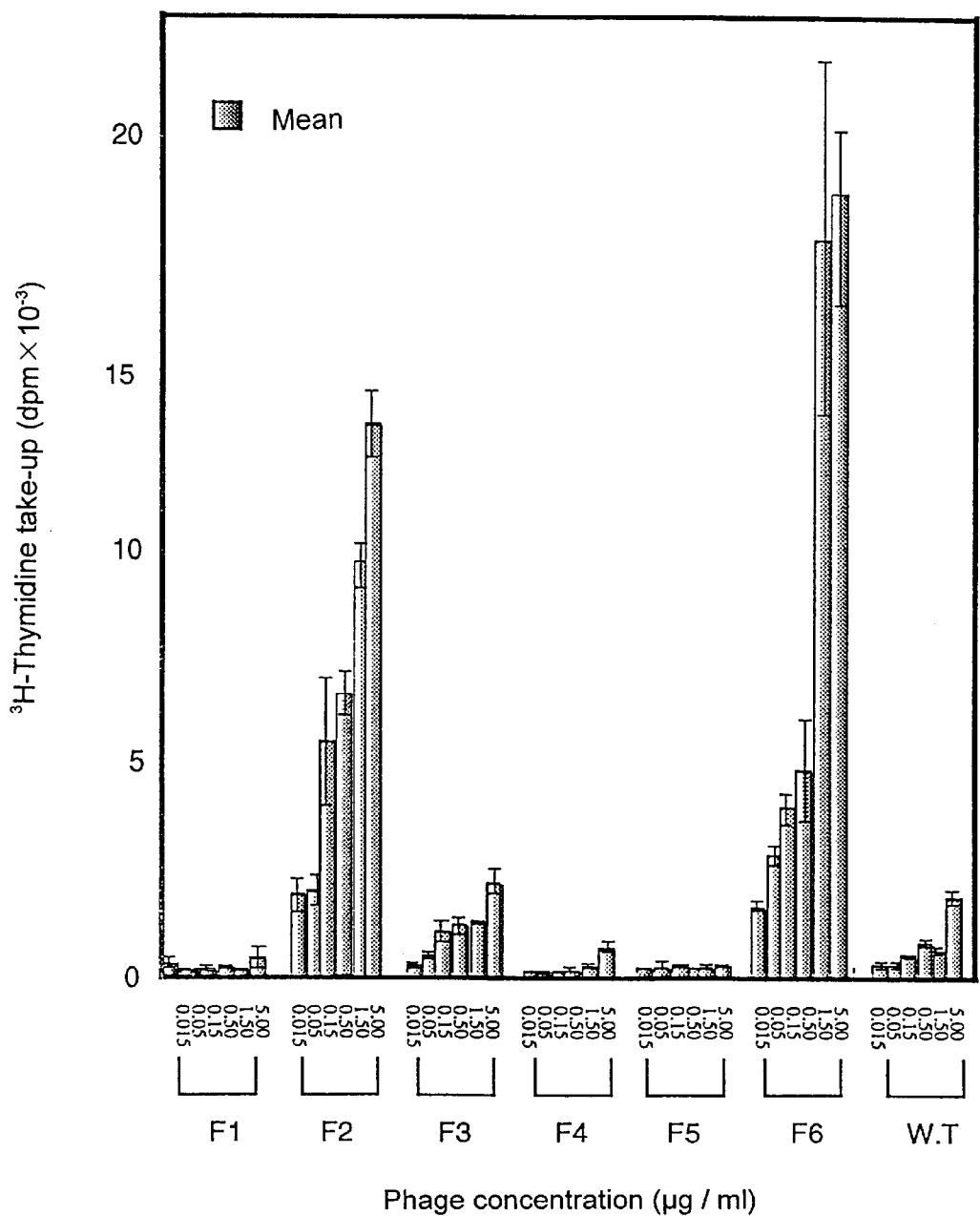
FIG. 4 shows effects of six phage clones on proliferation of mouse T cells.

First, for antigen, stimulation, BALB/c mice were administered intraperitoneally with 10 µg (200 µl/PBS) of phage (W. T.) not expressing pIII protein. Four weeks after the administration, spleen cells were removed from each mouse in the usual manner. The spleen cells were added to each well of 96-well culture plate at $1.5 \times 10^5$ cells/well. To each well was added purified W. T. or phages expressing any of F1 to F6 sequence at a final concentration of 0.015 to 5 µg/ml to make a total volume of 200 µl (RPMS 1640 medium containing 10% FCS) Triplicates were used for each sample. After incubating these samples on ice for 30 minutes, the cells were cultured under condition of 5% $CO_2$ at 37° C. for three days. Eighteen hours before completion of culture, the cells were pulse-labeled with [$^3$H]-thymidine (0.5 µCi/well). The cells were harvested with a cell harvester and a take-up of [$^3$H]-thymidine was measured with a liquid scintillation counter. As a result, as shown in FIG. 4, the growth of T cells observed with addition of phages expressing F1, F3, F4 or F5 sequence was approximately equivalent to that with W. T. phage. However, when phages expressing F2 or F6 sequence were added, it was found that the growth of T cells was enhanced by 5-fold to 10-fold as compared to W. T. phage. These results demonstrate that phages expressing F2 or F6 sequence have the activity to stimulate the growth of antigen-specific T cells.

Example 7
Binding Activity to mouse CD80 of Phages Expressing F2 or F6 Sequence

A binding activity to mouse CD80, a receptor of CTLA-4, of phages expressing F2 or F6 sequence which exhibited the activity to stimulate the growth of T cells in Example 5 was investigated.

Figure 5:
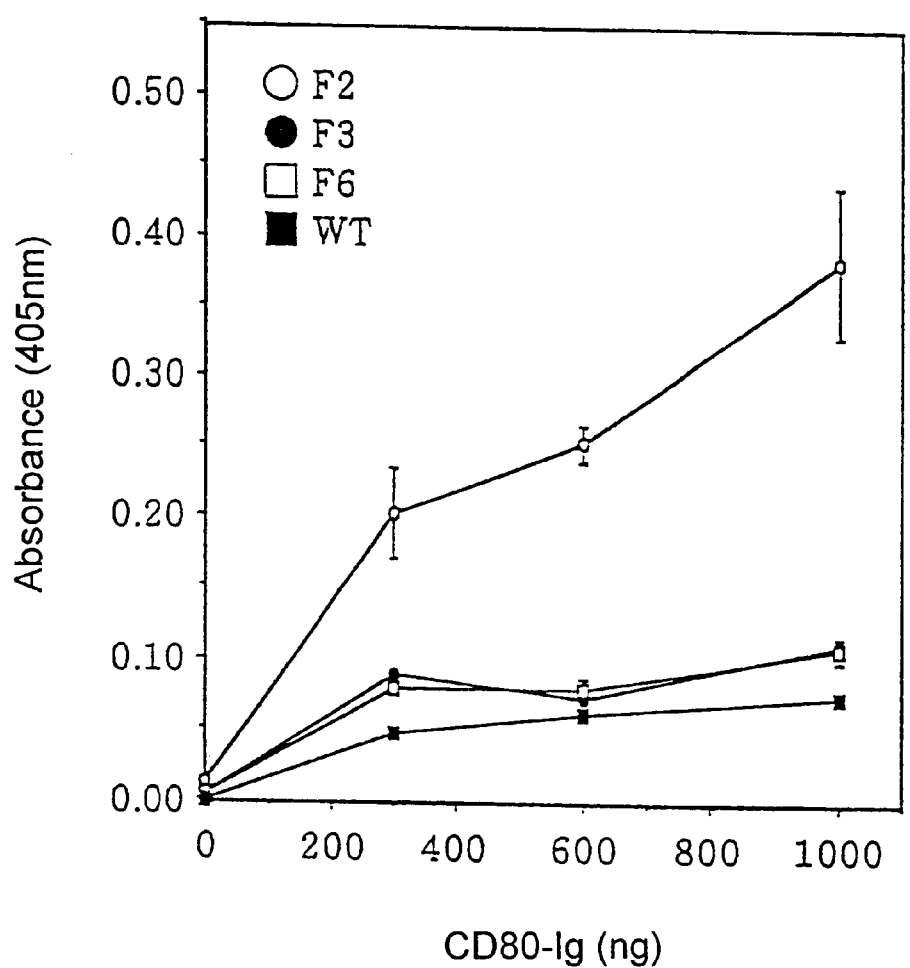
FIG. 5 shows a binding capacity of three phage clones to mouse BALB/c.

The binding activity was measured by ELISA. A 96-well ELISA plate (Sumitomo Bakelite, Tokyo) was coated with phages expressing F2 or F6 sequence ($4 \times 10^9$ virions/well/40 pi) at 4° C. overnight and then blocked with 50 mM Tris-HCl, pH 7.5, 150 mM NaCl (TBS) supplemented with 1% BSA at room temperature for 2 hours. After washing the plate with TBST, the plate was added with 200 to 1000 ng/35 µl of mouse CD80-Ig diluted with PBS and reacted at room temperature for 1 hour. After washing with TBST, the plate was reacted with alkali phosphatase-labeled anti-human IgG antibody (Zymet, California) diluted with TBS by 100-fold at room temperature for 1 hour. After washing, to the plate was added the substrate sodium p-nitrophenylphosphate hexahydrate and absorbance at 405 nm was measured. As a result, it was found that phage expressing F2 alone bound to mouse CD80-Ig in a concentration-dependent manner (FIG. 5).

Figure 6:
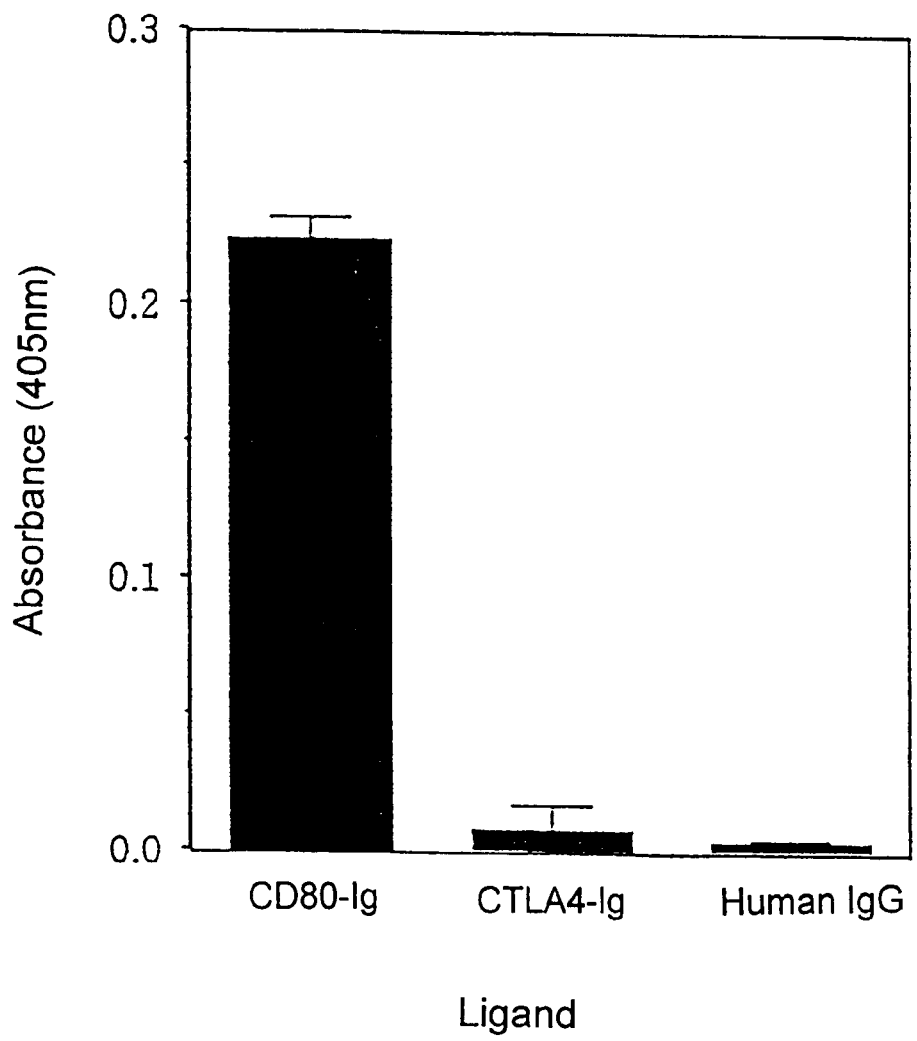
FIG. 6 shows a binding activity of phage clone expressing F2 sequence to mouse BALB/c, mouse CTLA-4 and human IgG.

Then, in order to prove binding specificity to CD80-Ig of the F2-expressing phage, a plate coated with phage expressing F2 sequence was reacted with mouse CD80-Ig, mouse CTLA-4-Ig and human IgG by ELISA as described in this Example. As a result, it was proved that phage expressing F2 sequence specifically reacted with mouse CD80-Ig (FIG. 6).

Example 8

Binding of Phage Expressing F2 Sequence with Human CD80-Ig

Example 7 demonstrated that the F2 phage specifically bound to mouse CD80-Ig. Then, whether phage expressing F2 sequence specifically binds to human CD80-Ig was investigated in this Example as described in Example 7, FIG. 5.

Figure 7:
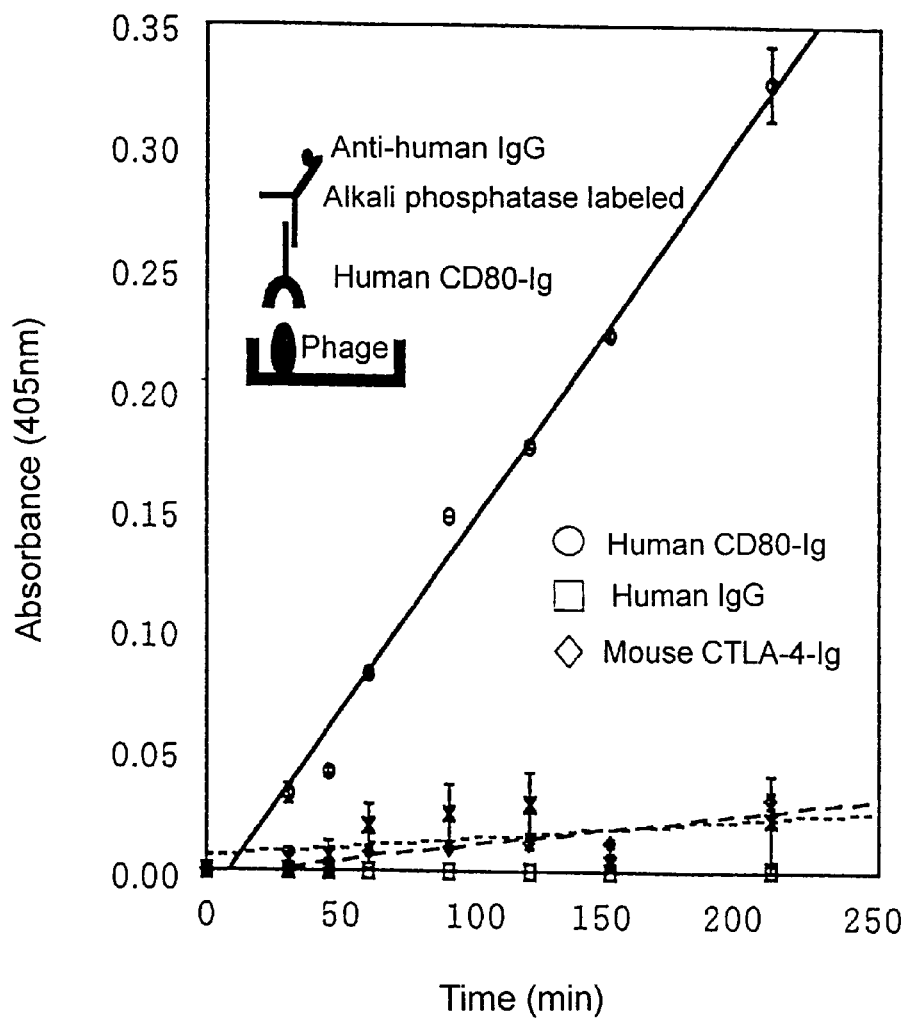
FIG. 7 shows a binding activity of phage clone expressing F2 sequence to human CD80-Ig.

Human CD80-Ig was prepared by constructing a fused gene of human CD80 extracellular domain and human Ig Cγ1 domain as described by Linsley et al. (J. Exp. Med. Vol. 173, p.721–730 (1991)). An expression plasmid pCDM8 incorporating the fused gene fragment was introduced into COS7 cells by DEAE-dextran method. After culturing for 72 hours, human CD80-Ig was purified from culture supernatant with Protein A Sepharose (Pharmacia). Using human CD80-Ig thus prepared, a binding activity of phage expressing F2 to human CD80-Ig was investigated with mouse CTLA-4-Ig and human IgG as negative control. As a result, likewise mouse CD80-Ig, it was proved that phage expressing F2 sequence specifically bound to human CD80-Ig as shown in FIG. 7. This indicates that phage expressing F2 sequence can effectively function for human immune system.

Example 9

T Cell Growth Stimulating Activity of Phages Expressing F2 or F6 Sequence to Mice Immunized with Egg Lysozyme Example 6 demonstrated that phages expressing F2 or F6 sequence exhibited the activity to stimulate the growth of T cells. In Example 6, there were used a phage protein as a primary antigen stimulation and the phage protein with expressed F2 or F6 sequence as a secondary stimulation in vitro. That is, in Example 6, a phage protein was used as an antigen and a secondary stimulation was made in a condition where both said antigen and F2 or F6 sequence are on the same particle. In this Example, however, the activity to stimulate the growth of T cells of phages expressing F2 or F6 as described in Example 6 was investigated wherein an antigen irrelevant to the phage (egg lysozyme) was used as a primary antigen stimulation and the egg lysozyme plus the phage particles expressing F2 or F6 sequence were separately added as a secondary stimulation.

Figure 8:
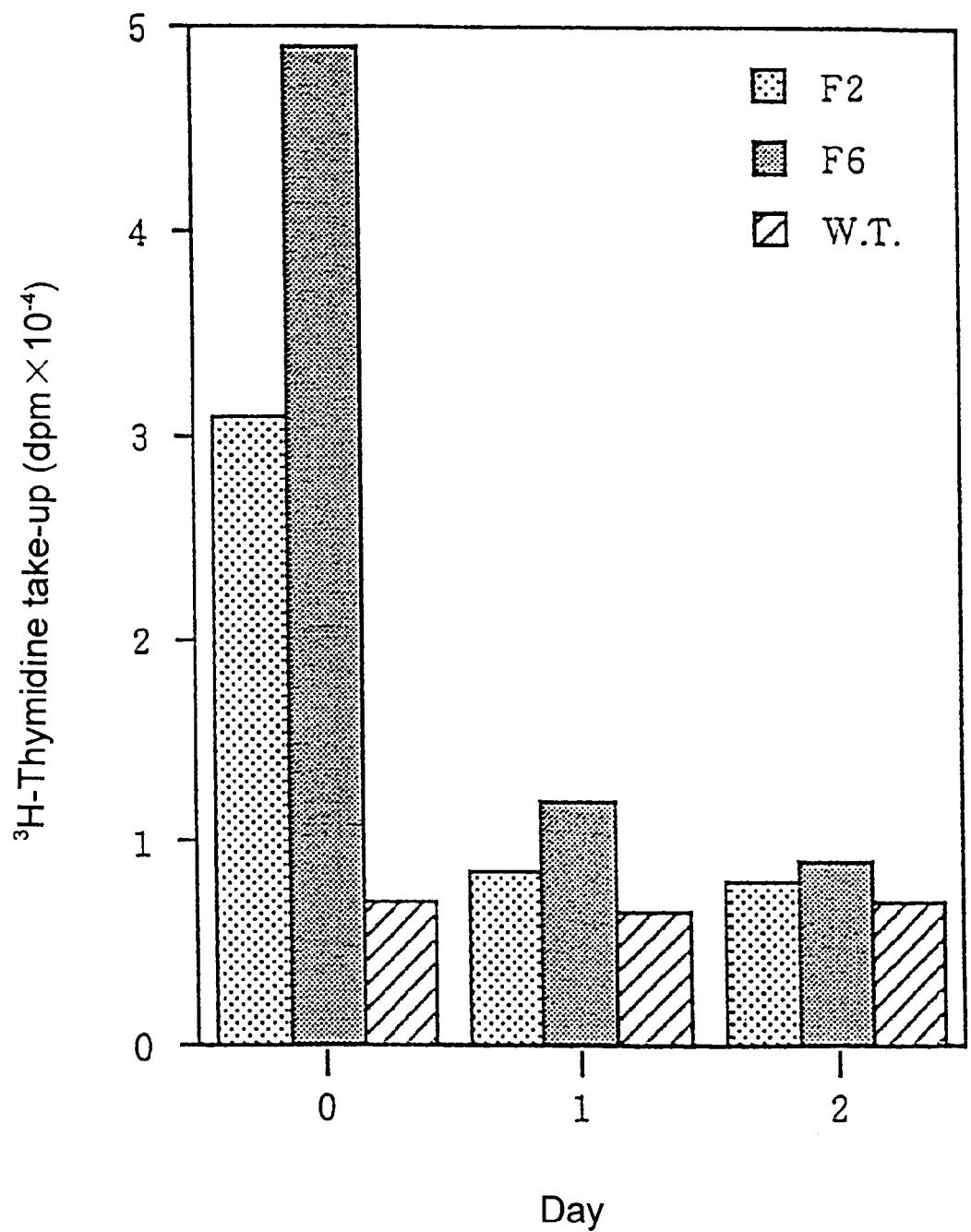
FIG. 8 shows a T cell growth-stimulating activity of phage clones expressing F2 or F6 sequence in mice immunized with egg lysozyme.

Egg lysozyme 10 μg (100 μl/Freund's incomplete adjuvant (FIA)) was subcutaneously injected to BALB/c mice. Four weeks after administration, spleen cells and the relevant lymph nodes were removed from each mouse in a usual manner. Each well of 96-well culture plate was added with the spleen cells at 1.5×105 cells/well and with egg lysozyme at 3 μg/ml. Phages expressing F2 or F6 sequence were added at 1 μg/ml either at the same time, 1 day after, or 2 days after, the addition of egg lysozyme. As a negative control, W. T. phage was added. Measurement after culture was as described in Example 6. As a result, as shown in FIG. 8, phages expressing F2 or F6 exhibited the antigen-specific activity to stimulate the growth of T cells even in case that a primary antigen stimulation was made with a non-phage derived antigen (in this case, egg lysozyme). Furthermore, it was found that the activity was exerted even if the antigen and F2 or F6 sequence were not on the same molecule and that a higher activity was obtained when the antigen and the phages were added simultaneously.

Example 10

Receptor Specificity of Phage Expressing F2 or F6 Sequence in T Cell Growth Stimulating Activity Each phage expressing F2 or F6 sequence reacted with anti-mouse CTLA-4 monoclonal antibody as shown in Example 5. Phage expressing F2 specifically bound to mouse CD80-Ig as shown in Example 7. Thus, in order to investigate whether the T cell growth stimulating activity of each phage expressing F2 or F6 as demonstrated in Example 9 is mediated through the receptor-ligand interaction, effects of CD80-Ig or CD86-Ig on the activity of each phage expressing F2 or F6 sequence were determined.

Egg lysozyme 50 μg (100 μl/PBS) was intraperitoneally administered to BALB/c mice. Four weeks after administration, spleen cells were removed from each mouse in a usual manner. In this Example, to each well of a 96-well culture plate were added the spleen cells at 1.5×10$^5$ cells/well and egg lysozyme at 3 μg/ml together with phage expressing F2 or F6 (1 μg/ml) and CD80-Ig or CD86-Ig or human Ig as a negative control at 0–1 μg/ml. The T cell growth stimulating activity was determined as described in Example 6.

Figure 9:
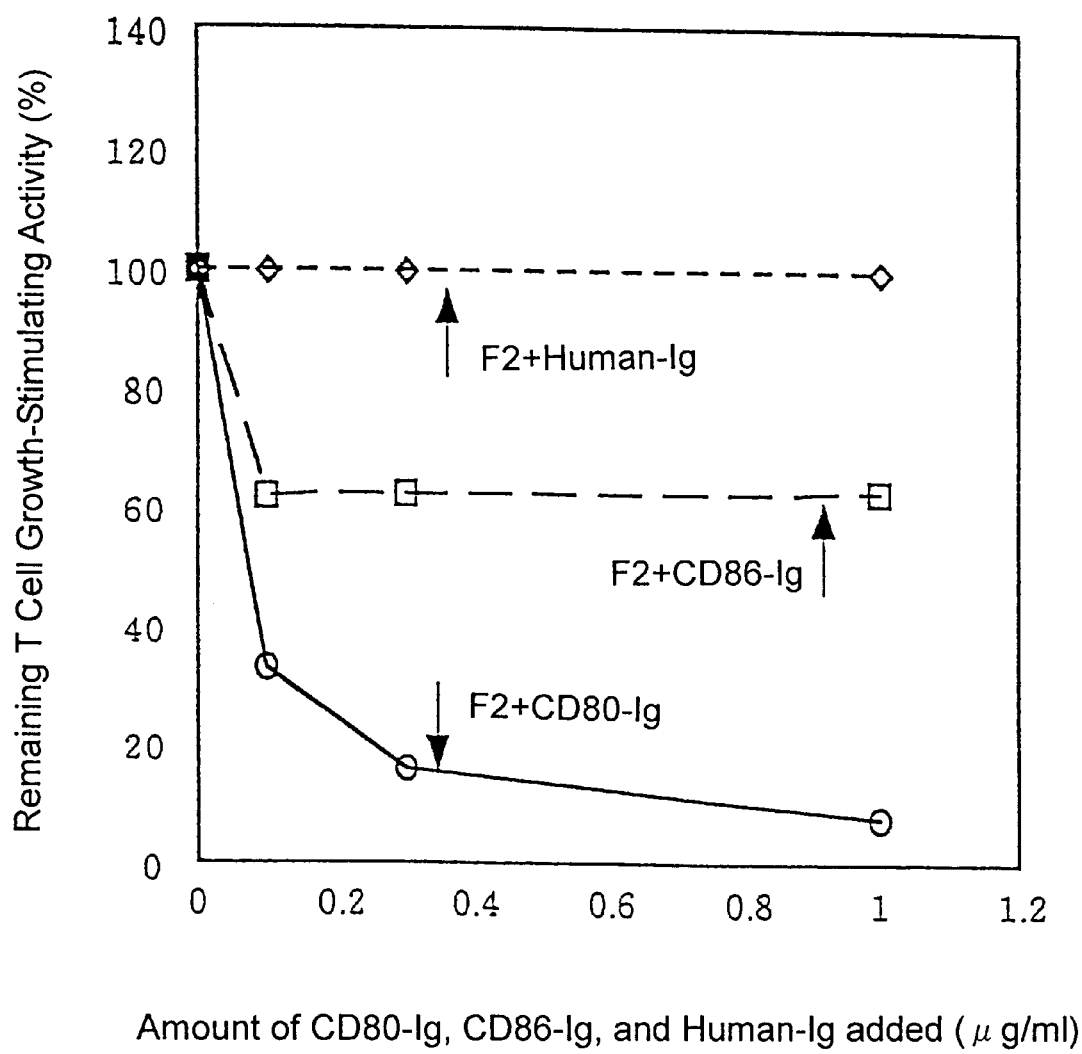
FIG. 9 shows effects of CD80-Ig and CD86-Ig on the T cell growth-stimulating activity of phage clone expressing F2 sequence.

As a result, as shown in FIG. 9, the T cell growth stimulating activity of phage expressing F2 sequence was greatly inhibited in the presence of CD-80Ig while the inhibition in the presence of CD86-Ig was approximately 40% of that in the presence of CD80-Ig. As reported by Mak et al. (Science, Vol.270, p.985 (1995)), excessive activation of T cells occurs in mice knockout in CTLA-4 gene to lead to animal death within 3–4 weeks after birth, suggesting inhibitory function of CTLA-4 molecule in the activation of T cells. In accordance with the report by Mak et al., the result obtained in this Example suggests that phage expressing F2 sequence induced T cell growth by blocking the interaction between CD80/CD86 and CTLA-4. In addition to such possibility that phage expressing F2 sequence blocked the negative activity of CTLA-4 molecule to the activation of T cells, there is another possibility that the phage bound to CD80/CD86 to give a positive signal for the activation of T cells through APC.

Figure 10:
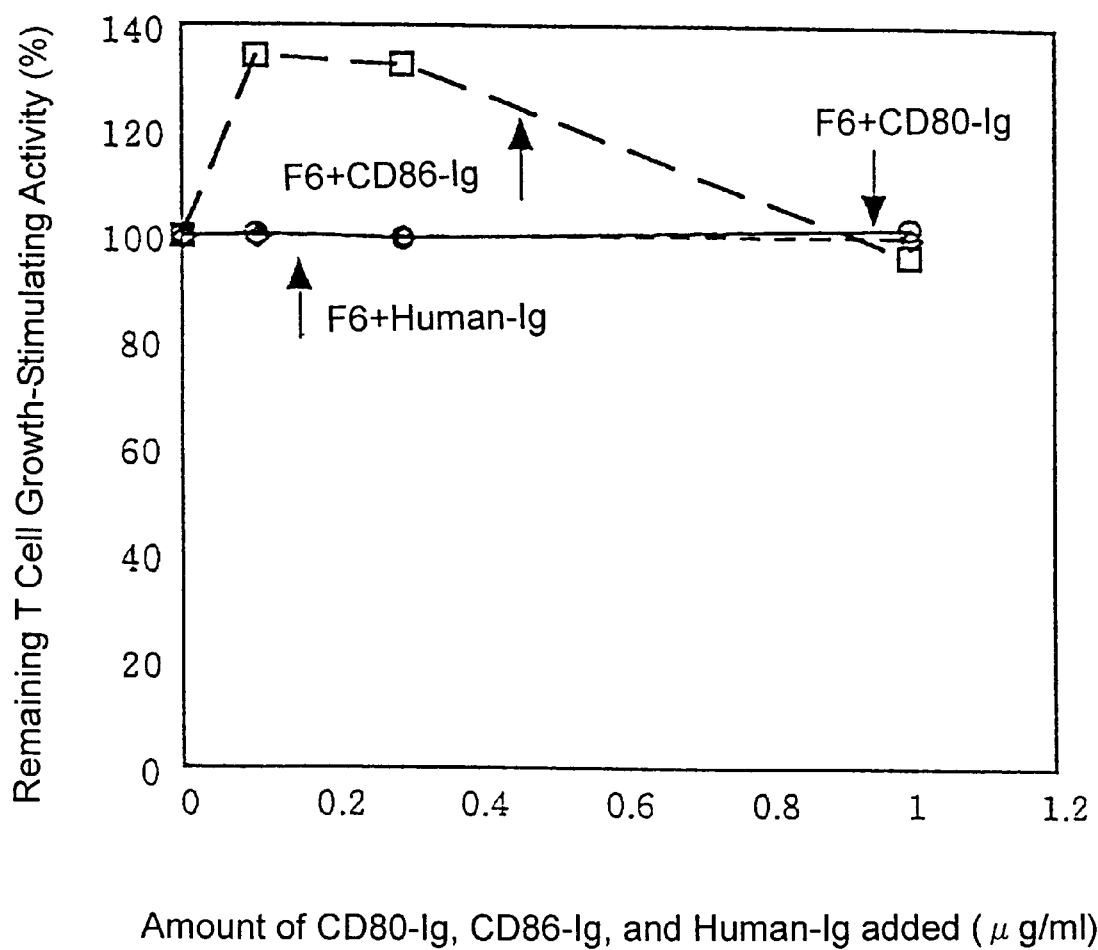
FIG. 10 shows effects of CD80-Ig and CD86-Ig on the T cell growth-stimulating activity of phage clone expressing F6 sequence.

On the other hand, the same experiment conducted for phage expressing F6 sequence revealed that addition of CD80-Ig or CD86-Ig did not inhibit the T cell growth stimulating activity as shown in FIG. 10, suggesting that phage expressing F6 sequence exhibits the activity through the binding to distinct molecule other than the receptor-ligand. This demonstrates that by screening phage random peptide library with an anti-ligand antibody, there can be obtained phages capable of reacting with unknown ligand- or receptor-like molecule resembling a target ligand and that the method of the invention is effective for screening unknown ligand or receptor.

Example 11

Anti-HBsAg Antibody Production Enhancing Activity of Phage Expressing F2 or F6 Sequence to Mice Immunized with HBsAg Example 9 demonstrated that phages expressing F2 or F6 sequence exhibit the activity to stimulate the growth of T cells to mice immunized with egg lysozyme to prove that the phages activate cells associated with the immune system even for foreign antigens. Thus, in order to investigate whether such activation of cells associated with the immune system also occurs with immunization with a vaccine antigen, the experiment was conducted with hepatitis B virus surface antigen (HBsAg).

BALB/c mice (four animals per group) were administered intraperitoneally with either 10 μg (100 μl/PBS) of recombinant HBsAg produced in yeast (yHBsAg; Juridical Foundation The Chemo-Sero-Therapeutic Research Institute) alone or in combination with phages expressing F2 or F6 (10: pg/100 μl). Fifteen days after primary immunization, th-e same samples were administered intraperitoneally., Three weeks after primary immunization, each mouse was bled. Serum was diluted with PBS-to 50-fold, 200-fold and 800-fold and then anti-HBsAg antibody titer was measured with Ausab EIA kit (Abbott Laboratories).

Figure 11:
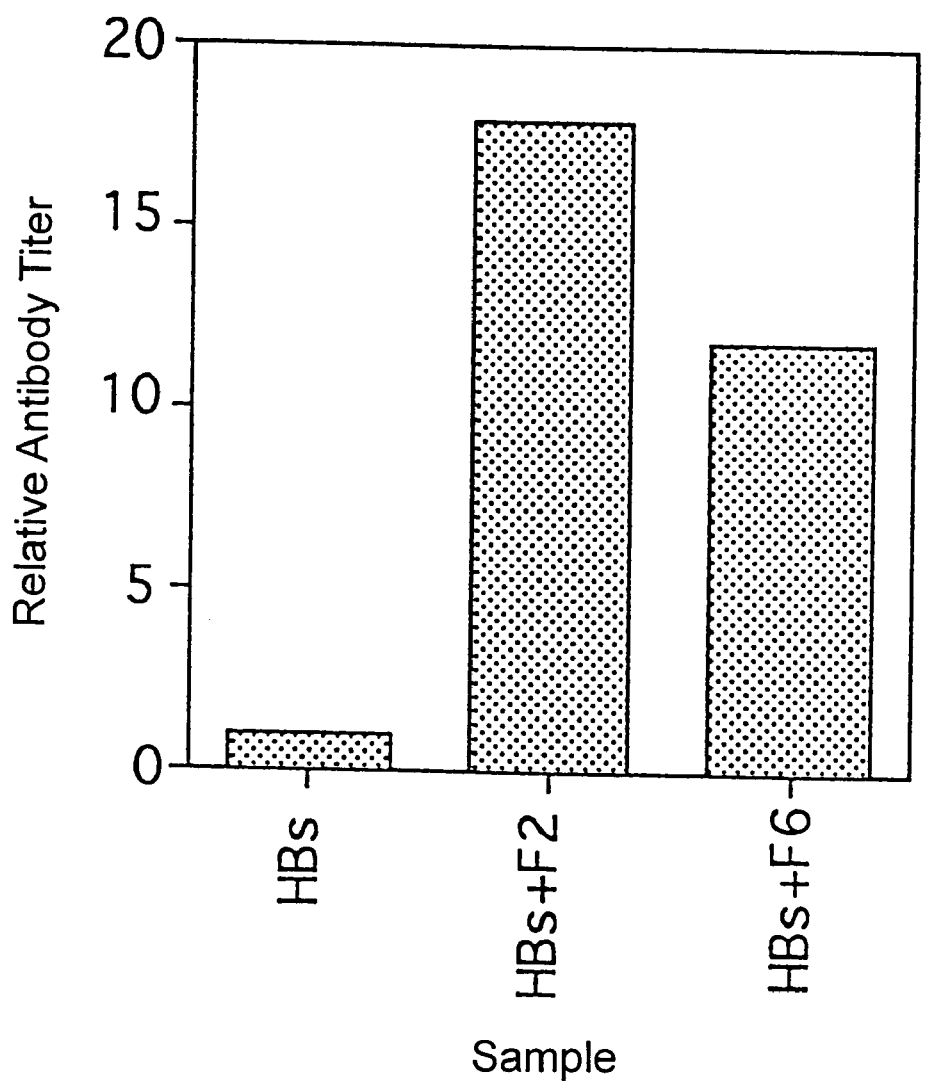
FIG. 11 shows the activity to enhance anti-HBs Ag antibody production of phage clones expressing F2 or F6 sequence.

The antibody titer was measured using a positive control attached to the kit as a standard. As a result, as shown in FIG. 11, when the anti-HBsAg antibody titer of the group immunized with HBsAg alone as shown in blood obtained three weeks after immunization is indicated as 1, the titer of the group immunized with yHBsAg together with phages expressing F2 or F6 sequence was indicated as 17.9 and 11.9, respectively, to prove a significantly higher titer of the latter group. This result revealed that phages expressing F2 or F6 sequence have an adjuvant activity.

What is claimed is:

1. An immunoregulatory molecule that stimulates the growth of T cells, is recognized by an anti-CTLA4 monoclonal antibody and comprises either SEQ ID NO:4 or SEQ ID NO:8.

2. The immunoregulatory molecule of claim 1, wherein said immunoregulatory molecule comprises SEQ ID NO:4.

3. The immunoregulatory molecule of claim 1, wherein said immunoregulatory molecule comprises SEQ ID NO:8.

4. An immunoregulatory molecule that is fixed on a carrier or incorporated into a protein, wherein said immunoregulatory molecule stimulates the growth of T cells, is recognized by an anti-CTLA4 monoclonal antibody and comprises either SEQ ID NO:4 or SEQ ID NO:8.

* * * * *

SEQUENCE LISTING

<160> NUMBER OF SEQ ID NOS: 8

<210> SEQ ID NO 1
<211> LENGTH: 432
<212> TYPE: PRT
<213> ORGANISM: bacteriophage(fd-tet)

<400> SEQUENCE: 1

```
Val Lys Lys Leu Leu Phe Ala Ile Pro Leu Val Val Pro Phe Tyr Ser
 1               5                  10                  15

His Ser Ala Asp Gly Ala Gly Ala Ala Gly Ala Glu Thr Val Glu Ser
                20                  25                  30

Cys Leu Ala Lys Pro His Thr Glu Asn Ser Phe Thr Asn Val Trp Lys
            35                  40                  45

Asp Asp Lys Thr Leu Asp Arg Tyr Ala Asn Tyr Glu Gly Cys Leu Trp
        50                  55                  60

Asn Ala Thr Gly Val Val Val Cys Thr Gly Asp Glu Thr Gln Cys Tyr
65                  70                  75                  80

Gly Thr Trp Val Pro Ile Gly Leu Ala Ile Pro Glu Asn Glu Gly Gly
                85                  90                  95

Gly Ser Glu Gly Gly Ser Glu Gly Gly Ser Glu Gly Gly Gly
                100                 105                 110

Thr Lys Pro Pro Glu Tyr Gly Asp Thr Pro Ile Pro Gly Tyr Thr Tyr
            115                 120                 125

Ile Asn Pro Leu Asp Gly Thr Tyr Pro Pro Gly Thr Glu Gln Asn Pro
        130                 135                 140

Ala Asn Pro Asn Pro Ser Leu Glu Glu Ser Gln Pro Leu Asn Thr Phe
145                 150                 155                 160

Met Phe Gln Asn Asn Arg Phe Arg Asn Arg Gln Gly Ala Leu Thr Val
                165                 170                 175

Tyr Thr Gly Thr Val Thr Gln Gly Thr Asp Pro Val Lys Thr Tyr Tyr
            180                 185                 190

Gln Tyr Thr Pro Val Ser Ser Lys Ala Met Tyr Asp Ala Tyr Trp Asn
        195                 200                 205

Gly Lys Phe Arg Asp Cys Ala Phe His Ser Gly Phe Asn Glu Asp Pro
        210                 215                 220

Phe Val Cys Glu Tyr Gln Gly Gln Ser Ser Asp Leu Pro Gln Pro Pro
225                 230                 235                 240

Val Asn Ala Gly Gly Gly Ser Gly Gly Ser Gly Gly Ser Glu
                245                 250                 255

Gly Gly Gly Ser Glu Gly Gly Ser Glu Gly Gly Ser Glu Gly
            260                 265                 270
```

```
Gly Gly Ser Gly Gly Ser Gly Ser Gly Asp Phe Asp Tyr Glu Lys
        275                 280                 285

Met Ala Asn Ala Asn Lys Gly Ala Met Thr Glu Asn Ala Asp Glu Asn
    290                 295                 300

Ala Leu Gln Ser Asp Ala Lys Gly Lys Leu Asp Ser Val Ala Thr Asp
305                 310                 315                 320

Tyr Gly Ala Ala Ile Asp Gly Phe Ile Gly Asp Val Ser Gly Leu Ala
                325                 330                 335

Asn Gly Asn Gly Ala Thr Gly Asp Phe Ala Gly Ser Asn Ser Gln Met
                340                 345                 350

Ala Gln Val Gly Asp Gly Asp Asn Ser Pro Leu Met Asn Asn Phe Arg
                355                 360                 365

Gln Tyr Leu Pro Ser Leu Pro Gln Ser Val Glu Cys Arg Pro Tyr Val
        370                 375                 380

Phe Gly Ala Gly Lys Pro Tyr Glu Phe Ser Ile Asp Cys Asp Lys Ile
385                 390                 395                 400

Asn Leu Phe Arg Gly Val Phe Ala Phe Leu Leu Tyr Val Ala Thr Phe
                405                 410                 415

Met Tyr Val Phe Ser Thr Phe Ala Asn Ile Leu Arg Asn Lys Glu Ser
                420                 425                 430

<210> SEQ ID NO 2
<211> LENGTH: 18
<212> TYPE: DNA
<213> ORGANISM: Artificial
<220> FEATURE:
<223> OTHER INFORMATION: Primer corresponding to nucleic acid sequence
      which codes for amino acid nos. 37 to 41 of SEQ ID NO:1

<400> SEQUENCE: 2
tgaattttct gtatgagg                                                18

<210> SEQ ID NO 3
<211> LENGTH: 15
<212> TYPE: PRT
<213> ORGANISM: Artificial
<220> FEATURE:
<223> OTHER INFORMATION: F1 amino acid sequence motif from phage random
      peptide library

<400> SEQUENCE: 3

Gly Leu His Ser Arg Cys His Ile Gly Arg Asp Cys Ser Ser Ala
1               5                   10                  15

<210> SEQ ID NO 4
<211> LENGTH: 15
<212> TYPE: PRT
<213> ORGANISM: Artificial
<220> FEATURE:
<223> OTHER INFORMATION: F2 amino acid sequence motif from phage random
      peptide library

<400> SEQUENCE: 4

Gly Phe Val Cys Ser Gly Ile Phe Ala Val Gly Val Gly Arg Cys
1               5                   10                  15

<210> SEQ ID NO 5
<211> LENGTH: 15
<212> TYPE: PRT
<213> ORGANISM: Artificial
<220> FEATURE:
<223> OTHER INFORMATION: F3 amino acid sequence motif from phage random
```

```
                peptide library

<400> SEQUENCE: 5

Ser Cys Val Phe His His Ser Gly Arg Tyr Trp Gly Arg Cys Val
1               5                   10                  15

<210> SEQ ID NO 6
<211> LENGTH: 15
<212> TYPE: PRT
<213> ORGANISM: Artificial
<220> FEATURE:
<223> OTHER INFORMATION: F4 amino acid sequence motif from phage random
      peptide library

<400> SEQUENCE: 6

His Tyr Gly Asp Cys Arg Tyr Asp Leu Gly Ser Cys Arg Gly Ala
1               5                   10                  15

<210> SEQ ID NO 7
<211> LENGTH: 15
<212> TYPE: PRT
<213> ORGANISM: Artificial
<220> FEATURE:
<223> OTHER INFORMATION: F5 amino acid sequence motif from phage random
      peptide library

<400> SEQUENCE: 7

Ala Cys Val Met Tyr Asp Phe Val Leu Arg Gly Met Cys Ala Arg
1               5                   10                  15

<210> SEQ ID NO 8
<211> LENGTH: 15
<212> TYPE: PRT
<213> ORGANISM: Artificial
<220> FEATURE:
<223> OTHER INFORMATION: F6 amino acid sequence motif from phage random
      peptide library

<400> SEQUENCE: 8

Ala Pro Gly Val Arg Leu Gly Cys Ala Val Leu Gly Arg Tyr Cys
1               5                   10                  15
```